United States Patent
Chen et al.

(10) Patent No.: US 10,610,117 B2
(45) Date of Patent: Apr. 7, 2020

(54) FLEXIBLE SILICON NANOWIRE ELECTRODE

(71) Applicant: INTERNATIONAL BUSINESS MACHINES CORPORATION, Armonk, NY (US)

(72) Inventors: Qianwen Chen, Yorktown Heights, NY (US); Huan Hu, Yorktown Heights, NY (US); Zheng Xu, Wappingers Falls, NY (US); Xin Zhang, Yorktown Heights, NY (US)

(73) Assignee: International Business Machines Corporation, Armonk, NY (US)

(*) Notice: Subject to any disclaimer, the term of this patent is extended or adjusted under 35 U.S.C. 154(b) by 272 days.

(21) Appl. No.: 15/803,210

(22) Filed: Nov. 3, 2017

(65) Prior Publication Data

US 2018/0220912 A1    Aug. 9, 2018

Related U.S. Application Data

(63) Continuation of application No. 15/424,265, filed on Feb. 3, 2017.

(51) Int. Cl.
*A61B 5/0408* (2006.01)
*A61B 5/00* (2006.01)
(Continued)

(52) U.S. Cl.
CPC .......... *A61B 5/0408* (2013.01); *A61B 5/0478* (2013.01); *A61B 5/0492* (2013.01);
(Continued)

(58) Field of Classification Search
CPC .......... B82Y 5/00; B82Y 15/00; B82Y 40/00; Y10S 977/762; Y10S 977/84;
(Continued)

(56) References Cited

U.S. PATENT DOCUMENTS

| | | | |
|---|---|---|---|
| 8,333,874 B2 | 12/2012 | Currie | |
| 9,173,583 B2 | 11/2015 | Chen et al. | |
| 9,283,386 B2 | 3/2016 | Park et al. | |
| 2004/0054393 A1 | 3/2004 | Stemme et al. | |

(Continued)

OTHER PUBLICATIONS

List of IBM Patents or Patent Applications Treated as Related dated Nov. 3, 2017, 2 pages.
(Continued)

*Primary Examiner* — Peter Dungba Vo
*Assistant Examiner* — Joshua D Anderson
(74) *Attorney, Agent, or Firm* — Tutunjian & Bitetto, P.C.; Erik Johnson

(57) ABSTRACT

A method is presented for forming a nanowire electrode. The method includes forming a plurality of nanowires over a first substrate, depositing a conducting layer over the plurality of nanowires, forming solder bumps and electrical interconnections over a second flexible substrate, and integrating nanowire electrode arrays to the second flexible substrate. The plurality of nanowires are silicon (Si) nanowires, the Si nanowires used as probes to penetrate skin of a subject to achieve electrical biopotential signals. The plurality of nanowires are formed over the first substrate by metal-assisted chemical etching.

5 Claims, 6 Drawing Sheets

(51) Int. Cl.
*A61B 5/0478* (2006.01)
*A61B 5/0492* (2006.01)
*A61B 5/0496* (2006.01)
*B82Y 40/00* (2011.01)

(52) U.S. Cl.
CPC ............ *A61B 5/0496* (2013.01); *A61B 5/685* (2013.01); *B82Y 40/00* (2013.01); *A61B 2562/0209* (2013.01); *A61B 2562/0285* (2013.01); *A61B 2562/12* (2013.01); *A61B 2562/125* (2013.01); *Y10S 977/762* (2013.01)

(58) Field of Classification Search
CPC ............ Y10S 977/843; Y10S 977/844; Y10S 977/889; Y10S 977/89; Y10S 977/891; Y10S 977/892; A61B 5/0408; A61B 5/0478; A61B 5/0492; A61B 5/0496; A61B 5/685; A61B 2562/0209; A61B 2562/0285; A61B 2562/125; B05D 1/12; B05D 1/36; B05D 5/12; C23C 18/1262
USPC ............ 472/97.1, 122, 123, 180, 197, 203; 216/99, 100, 103, 106, 107, 108, 109; 438/750, 753, 754
See application file for complete search history.

(56) References Cited

U.S. PATENT DOCUMENTS

| | | |
|---|---|---|
| 2008/0009763 A1* | 1/2008 | Chiou .................. A61B 5/0408 600/373 |
| 2008/0139911 A1* | 6/2008 | Chandrasekaran .. A61B 5/0408 600/382 |
| 2009/0299213 A1 | 12/2009 | Patolsky et al. |
| 2012/0214066 A1* | 8/2012 | Miller .................... B82Y 30/00 429/219 |
| 2012/0283538 A1 | 11/2012 | Rose et al. |
| 2013/0041235 A1 | 2/2013 | Rogers et al. |
| 2015/0173673 A1 | 6/2015 | Toth et al. |
| 2015/0367122 A1 | 12/2015 | Morshed et al. |
| 2016/0128588 A1 | 5/2016 | Melosh et al. |

OTHER PUBLICATIONS

Robinson et al., "Vertical nanowire electrode arrays as a scalable platform for intracellular interfacing to neuronal circuits", Nature Nanotechnology Letters, Jan. 10, 2012. DOI: 10.1038/nnano.2011.249. pp. 180-184.

Celik et al., "Graphene-Enabled Electrodes for Electrocardiogram Monitoring", Nanomaterials 2016, vol. 6, Issue 9. Aug. 23, 2016. DOI: 10.3390/nano6090156. pp. 1-16.

* cited by examiner

FLEXIBLE SILICON NANOWIRE ELECTRODE

BACKGROUND

Technical Field

The present invention relates generally to nanowire devices, and more specifically, to a flexible silicon nanowire electrode.

Description of the Related Art

Measuring biopotential signals, such as electrocardiogram (ECG), electroencephalogram (EEG), electrooculogram (EOG), and electromyogram (EMG) signals, is significant for both research and clinical applications. Changes in these electrical biopotential signals can be used to record heart rate, assess muscle contraction, mechanics or inferring movement rates across the muscle, study brain activity, etc. All these measurements can be very useful in basic physiology, behavioral or pharmacological/toxicology studies.

Electrodes are key components for continuous physiological monitoring. Conventional wet electrodes, which usually require skin preparation and the use of conductive gels to reduce skin-sensor interface impedance, can be uncomfortable for many users.

SUMMARY

In accordance with an embodiment, a method is presented for forming a nanowire electrode. The method includes forming a plurality of nanowires over a first substrate, depositing a conducting layer over the plurality of nanowires, forming electrical interconnections and solder bumps over the second flexible substrate, and integrating nanowire electrode arrays to the flexible substrate. The plurality of nanowires are silicon (Si) nanowires, the Si nanowires used as probes to penetrate skin of a subject to achieve electrical biopotential signals. The plurality of nanowires are formed over the first substrate by metal-assisted chemical etching, and bio-compatible conductive coating and high-doped substrate are used to improve mechanical strength of electrodes and achieve low-impedance electrodes, respectively.

In accordance with an embodiment, a flexible silicon nanowire electrode structure is provided. The nanowire electrode structure includes a plurality of silicon (Si) nanowires formed by metal-assisted chemical etching on a first substrate, the plurality of Si nanowires coated with a conducting layer and a plurality of nanowire chips integrated within a second substrate, the second substrate being a flexible substrate contacting solder bumps formed adjacent the first substrate. The plurality of Si nanowires are used as probes to penetrate skin of a subject.

It should be noted that the exemplary embodiments are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be described within this document.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The invention will provide details in the following description of preferred embodiments with reference to the following figures wherein.

Throughout the drawings, same or similar reference numerals represent the same or similar elements.

DETAILED DESCRIPTION

Figure 1:
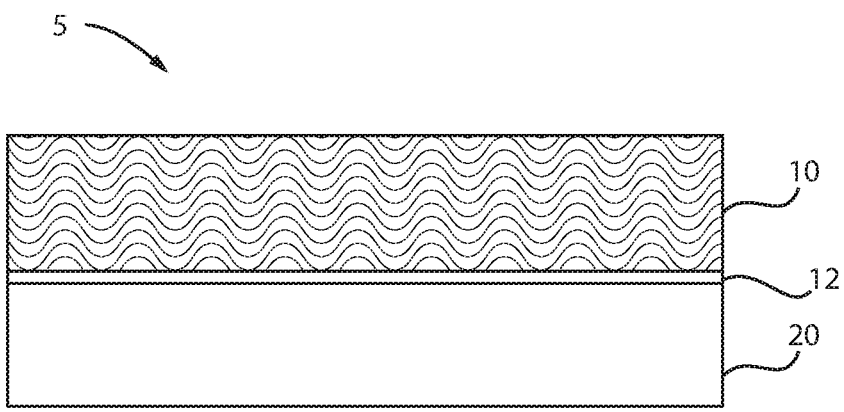
FIG. 1 is a cross-sectional view of a semiconductor structure having a substrate attached to a glass handler, in accordance with an embodiment of the present invention.

In one or more embodiments, a method is presented for forming a nanowire electrode. The method includes forming a plurality of nanowires over a first substrate, depositing a conducting layer over the plurality of nanowires, forming solder bumps adjacent the first substrate, the solder bumps in opposed relation to the plurality of nanowires, and forming a second substrate adjacent the solder bumps, the second substrate including interconnection lines in electrical communication with the solder bumps. The plurality of nanowires are silicon (Si) nanowires, the Si nanowires used as probes to penetrate skin of a subject. The plurality of nanowires are formed over the first substrate by metal-assisted chemical etching.

In one or more embodiments, a nanowire electrode is provided. The nanowire electrode includes a plurality of nanowires formed over a first substrate, a conducting layer deposited over the plurality of nanowires, solder bumps formed adjacent the first substrate and in opposed relation to the plurality of nanowires, and a second substrate formed adjacent the solder bumps, the second substrate including interconnection lines in electrical communication with the solder bumps.

In one or more embodiments, a nanowire electrode structure is provided. The nanowire electrode structure includes a plurality of silicon (Si) nanowires formed by metal-assisted chemical etching on a first substrate, the plurality of Si nanowires coated with a conducting layer and a plurality of nanowire chips integrated within a second substrate, the second substrate being a flexible substrate contacting solder bumps formed adjacent the first substrate. The plurality of Si nanowires are used as probes to penetrate skin of a subject. The plurality of Si nanowires penetrate at least a stratum basale layer (or Stratum Germinativum (SG) layer) of the skin of the subject.

In one or more embodiments, silicon nanowires are used to penetrate the electrically conducting Stratum Germinativum (SG) layer of the skin to circumvent the high impedance at the skin-sensor interface. The assembly includes solid electrode arrays formed on a flexible substrate to construct large-area flexible nanowire electrodes. The methods use a high-doped silicon substrate and metal over-coating to construct low impedance nanowire electrodes. The methods further use a bio-compatible metal over-coating on the formed silicon nanowires to improve the mechanical strength of the nanowire electrodes. The methods further use a low-temperature assembly approach to integrate multi-layers and structures.

In one or more embodiments, silicon nanowires are formed by metal-assisted chemical etching on a silicon wafer. These nanowires are used to penetrate at least the electrically conducting Stratum Germinativum (SG) layer of the skin to circumvent the high impedance at the skin-sensor interface. By using an array of nanowires on a flexible substrate, a flexible silicon nanowire electrode for at least clinical applications can be achieved. The nanowire electrode techniques described herein can be used to measure, e.g., at least electroencephalogram (EEG) signals, electrocardiogram (ECG) signals, electrooculography (EOG) signals, and/or electromyography (EMG) signals.

In one or more embodiments, the silicon nanowires have a length of about 10-100 um and a diameter of about 10 nm to 1 um for use as electrodes/probes. The silicon nanowires are formed over a thin silicon substrate on top of a flexible polymer substrate to achieve flexible electrode patches. Additionally, the silicon nanowires include a bio-compatible metal over-coating to prevent, e.g., skin irritation.

In one or more embodiments, highly-doped silicon nanowires are integrated with a metal over-coating to construct low resistance nanowire electrodes/probes. Additionally, solid silicon nanowire chips are integrated on a flexible polymer substrate to make flexible electrodes for clinical application. The bio-compatible low-temperature assembly methods use low-temperature wafer bonding, glass handler releasing, wafer transfer, and low-temperature solder bump bonding to achieve multi-layer integration.

In one or more embodiments, silicon nanowires are used as a probe. Fabrication of the silicon nanowires is accomplished by a wet etching method referred to as metal-assisted chemical etching, which results in a low-temperature assembly approach to integrate nanowire arrays on a flexible substrate. The silicon nanowires are of a sub-micro width to be used as probes to penetrate human skin. In one or more embodiments, the silicon nanowires are directly etched on a silicon semiconductor layer and the nanowire structure is built by using a conductive silicon substrate, metal coating over the nanowires, and backside metal bump to achieve electrical connections to nanowire chips formed within or embedded within a flexible substrate. The silicon nanowires act as a penetrating probe to penetrate the skin of a subject for more accurate and sensitive signal measurement.

As used herein, "semiconductor device" refers to an intrinsic semiconductor material that has been doped, that is, into which a doping agent has been introduced, giving it different electrical properties than the intrinsic semiconductor. Doping involves adding dopant atoms to an intrinsic semiconductor, which changes the electron and hole carrier concentrations of the intrinsic semiconductor at thermal equilibrium. Dominant carrier concentration in an extrinsic semiconductor determines the conductivity type of the semiconductor.

As used herein, the term "drain" means a doped region in the semiconductor device located at the end of the channel, in which carriers are flowing out of the transistor through the drain.

As used herein, the term "source" is a doped region in the semiconductor device, in which majority carriers are flowing into the channel.

The term "direct contact" or "directly on" means that a first element, such as a first structure, and a second element, such as a second structure, are connected without any intermediary conducting, insulating or semiconductor layers at the interface of the two elements.

The terms "overlying", "atop", "positioned on" or "positioned atop" means that a first element, such as a first structure, is present on a second element, such as a second structure, wherein intervening elements, such as an interface structure can be present between the first element and the second element.

The term "electrically connected" means either directly electrically connected, or indirectly electrically connected, such that intervening elements are present; in an indirect electrical connection, the intervening elements can include inductors and/or transformers.

The term "crystalline material" means any material that is single-crystalline, multi-crystalline, or polycrystalline.

The term "non-crystalline material" means any material that is not crystalline; including any material that is amorphous, nano-crystalline, or micro-crystalline.

The term "intrinsic material" means a semiconductor material which is substantially free of doping atoms, or in which the concentration of dopant atoms is less than $10^{15}$ atoms/cm$^3$.

As used herein, "p-type" refers to the addition of impurities to an intrinsic semiconductor that creates deficiencies of valence electrons. In a silicon-containing substrate, examples of n-type dopants, i.e., impurities, include but are not limited to: boron, aluminum, gallium and indium.

As used herein, "n-type" refers to the addition of impurities that contributes free electrons to an intrinsic semiconductor. In a silicon containing substrate examples of n-type dopants, i.e., impurities, include but are not limited to antimony, arsenic and phosphorous.

As used herein, an "anisotropic etch process" denotes a material removal process in which the etch rate in the direction normal to the surface to be etched is greater than in the direction parallel to the surface to be etched. The anisotropic etch can include reactive-ion etching (RIE). Other examples of anisotropic etching that can be used include ion beam etching, plasma etching or laser ablation.

The term "processing" as used herein includes deposition of material or photoresist, patterning, exposure, development, etching, cleaning, stripping, implanting, doping, stressing, layering, and/or removal of the material or photoresist as required in forming a described structure.

As used herein, "depositing" can include any now known or later developed techniques appropriate for the material to be deposited including but not limited to, for example: chemical vapor deposition (CVD), low-pressure CVD (LPCVD), plasma-enhanced CVD (PECVD), semi-atmosphere CVD (SACVD) and high density plasma CVD (HDPCVD), rapid thermal CVD (RTCVD), ultra-high vacuum CVD (UHVCVD), limited reaction processing CVD (LRPCVD), metal-organic CVD (MOCVD), sputtering deposition, ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating, evaporation.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

It is to be understood that the present invention will be described in terms of a given illustrative architecture; however, other architectures, structures, substrate materials and process features and steps/blocks can be varied within the scope of the present invention. It should be noted that certain features cannot be shown in all figures for the sake of clarity. This is not intended to be interpreted as a limitation of any particular embodiment, or illustration, or scope of the claims.

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this invention.

The present subject matter will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In the art of nanotechnology, nanowires are usually interpreted as nanostructures having a lateral size (e.g., diameter for cylindrical nanowires or width for pyramidal or hexagonal nanowires) of nano-scale or nanometer dimensions, whereas its longitudinal size is unconstrained. Such nanostructures are commonly also referred to as nanowhiskers, one-dimensional nano-elements, nanorods, nanotubes, etc. Generally, nanowires with a polygonal cross section are considered to have at least two dimensions each of which are not greater than 300 nm. However, the nanowires can have a diameter or width of up to about 1 μm. The one dimensional nature of the nanowires provides unique physical, optical and electronic properties. These properties can for example be used to form devices utilizing quantum mechanical effects (e.g., using quantum wires) or to form heterostructures of compositionally different materials that usually cannot be combined due to large lattice mismatch. As the term "nanowire" implies, the one dimensional nature is often associated with an elongated shape. In other words, "one dimensional" refers to a width or diameter less than 1 micron and a length greater than 1 micron. Since nanowires can have various cross-sectional shapes, the diameter is intended to refer to the effective diameter. By effective diameter, it is meant the average of the major and minor axis of the cross-section of the structure.

A nanowire, as the semiconducting region, can be manufactured by a variety of processes. Depending on the actual geometry of wrapped carbon sheets forming a nanotube, the electric properties can be metallic, insulating or semiconducting. Hence, a nanotube can serve as a nanowire in certain embodiments of the present invention. Further, nanowires can be produced by lithography on a semiconductor substrate or other conventional methods. The cross-sectional geometry of the nanowire, in principle, is irrelevant. Therefore, one can fabricate nanowires having regular cross-section as well as wires having irregular geometries. Further, a corresponding semiconductor nanowire can be engineered to be an n-type or a p-type semiconductor.

Nanowire semiconductor devices include a nanowire formed from a semiconductor material. The channel region of the nanowire is often suspended above a substrate such that the gate materials surround the channel region of the nanowire. This forms a gate-all-around device where the gate is arranged 360 degrees about the channel region. Nanowires can be stacked vertically to increase the density of the field effect transistor (FET) devices on the substrate. Metal oxide semiconductor field effect transistor (MOSFET) devices such as p-type (pFET) and n-type (nFET) devices are often formed from different semiconductor materials. For example, nFET devices having a silicon channel region and pFET devices having silicon germanium channel regions offer performance advantages in complementary metal oxide semiconductor (CMOS) devices.

Nanowires made of silicon (Si) are especially attractive because of silicon's compatibility with existing integrated circuit (IC) processes. Moreover, the chemical and physical properties of silicon can be controlled to adjust the device sensitivity, and silicon nanowires can be selectively grown. Using silicon allows the vast knowledge of silicon technology to be applied to applications such as sensing. Using semiconductor nanowires, researchers have demonstrated electrical sensors for biological and chemical species, and designed a range of nano-electronic and photonic devices in different material systems. In many of these demonstrations, nanowires were assembled after growth into parallel or crossed arrays by alignment aided by fluid flow or by applying electric fields. In other cases, electrical contacts were defined with electron-beam lithography on a few selected nanowires.

Silicon (Si) nanowires, with unique physio-chemical properties, have brought significant breakthroughs in fields such as electronic devices, biochemical sensors, thermoelectric devices, solar cells, and electrochemical energy conversion and storage devices. In some cases, single crystalline silicon nanowires are preferred over polycrystalline (poly-Si) and amorphous silicon (a-Si) nanowires for use in the applications of electronic devices, biochemical sensors and thermoelectric devices, because they can have fewer defects and can be stronger and more conductive than polycrystalline and amorphous silicon nanowires of similar diameter.

FIG. 1 is a cross-sectional view of a semiconductor structure having a substrate attached to a glass handler, in accordance with an embodiment of the present invention.

A semiconductor structure 5 includes a semiconductor substrate 10 attached to a glass handler 20 via an adhesive bonding layer 12.

In one example embodiment, high-doped silicon (e.g., 0.001-0.005 Ohm-cm resistance) can be used to form substrate 10 for low impedance electrodes. The bonding layer 12 can be applied by a low temperature bonding method, such as adhesive bonding, which can be used to join the substrate 10 to the glass handler 20. A glass wafer can be used as the handler 20 for process compatibility.

In one or more embodiments, the substrate 10 can be a semiconductor or an insulator with an active surface semiconductor layer. The substrate 10 can be crystalline, semi-crystalline, microcrystalline, or amorphous. The substrate 10 can be essentially (i.e., except for contaminants) a single element (e.g., silicon), primarily (i.e., with doping) of a single element, for example, silicon (Si) or germanium (Ge), or the substrate 10 can include a compound, for example, $Al_2O_3$, $SiO_2$, GaAs, SiC, or SiGe. The substrate 10 can also have multiple material layers, for example, a semiconductor-on-insulator substrate (SeOI), a silicon-on-insulator substrate (SOI), germanium-on-insulator substrate (GeOI), or silicon-germanium-on-insulator substrate (SGOI). The substrate 10 can also have other layers forming the substrate 10, including high-k oxides and/or nitrides. In one or more embodiments, the substrate 10 can be a silicon wafer. In an embodiment, the substrate 10 is a single crystal silicon wafer.

Figure 2:
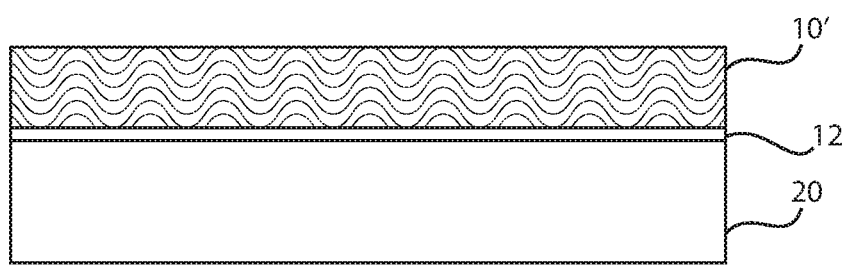
FIG. 2 is a cross-sectional view of the semiconductor structure of FIG. 1 where the substrate is thinned, in accordance with an embodiment of the present invention.

FIG. 2 is a cross-sectional view of the semiconductor structure of FIG. 1 where the substrate is thinned, in accordance with an embodiment of the present invention.

In various embodiments, the substrate 10 can be thinned to a desired thickness to form substrate 10'. The desired thickness can be about 10-100 μm, which is equivalent to the thickness of the stratum corneum layer of skin. In one example, mechanical grinding and chemical-mechanical polishing can be used to thin or etch the substrate 10 to form substrate 10'.

In one embodiment, the etch process can be an anisotropic etch process, such as reactive ion etch (RIE). The etching can include a dry etching process such as, for example, reactive ion etching, plasma etching, ion etching or laser ablation. The etching can further include a wet chemical etching process in which one or more chemical etchants are used to remove portions of the blanket layers that are not protected by the patterned photoresist. The patterned photoresist can be removed utilizing an ashing process.

In various embodiments, the height of the substrate can be selectively reduced or thinned by chemical-mechanical polishing (CMP) and/or etching. Therefore, the planarization process can be provided by CMP. Other planarization process can include grinding and polishing.

As used herein, the term "selective" in reference to a material removal process denotes that the rate of material removal for a first material is greater than the rate of removal for at least another material of the structure to which the material removal process is being applied. For example, in one embodiment, a selective etch can include an etch chemistry that removes a first material selectively to a second material by a ratio of 10:1 or greater, e.g., 100:1 or greater, or 1000:1 or greater.

Figure 3:
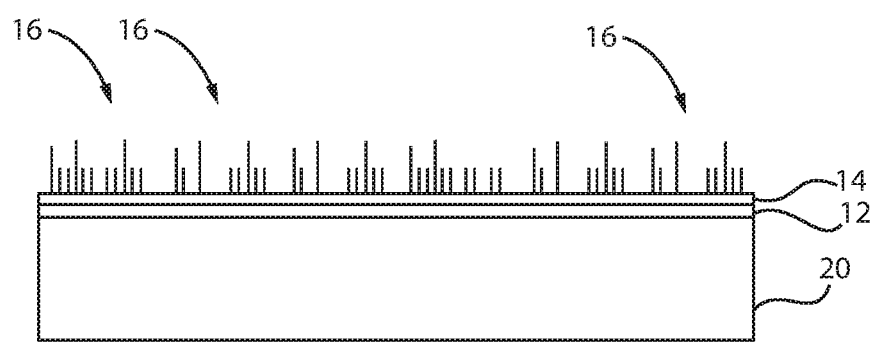
FIG. 3 is a cross-sectional view of the semiconductor structure of FIG. 2 where metal-assisted chemical etching takes place to form a plurality of silicon (Si) nanowires on a Si wafer, in accordance with an embodiment of the present invention.

FIG. 3 is a cross-sectional view of the semiconductor structure of FIG. 2 where metal-assisted chemical etching takes place to form a plurality of silicon (Si) nanowires on a Si wafer, in accordance with an embodiment of the present invention.

In various embodiments, silicon nanowires 16 are formed over the remaining substrate 14 by dipping the substrate 10' into chemicals for several minutes to perform metal-assisted chemical etching.

Metal-assisted chemical etching offers a method of etching silicon by patterning a silicon surface with a layer of metal. The metal acts as a catalyst for etching the silicon surface directly beneath it when exposed to an oxidizing agent (e.g., $H_2O_2$) and an acid (e.g., HF). Metal-assisted chemical etching can produce nanowires of high aspect ratios in silicon. Since it is a wet etch, metal-assisted chemical etching can easily be done in large quantities for a low price compared to popular dry etch methods that can require a vacuum or plasma. Also, the ability to make structures that are undamaged in any shape capable of being patterned with metal (e.g., gold) has made metal-assisted chemical etching a viable method of silicon nanowire fabrication.

Metal-assisted chemical etching is an electroless chemical etching technique that can etch micron (e.g., about 1-1000 μm), sub-micron (e.g., about 0.1-1 μm), and nano-sized (e.g., 0.5-100 nm) features in substrates or wafers with high aspect ratios. Metal-assisted chemical etching uses a non-spherical metal catalyst deposited onto a substrate to locally increase the dissolution rate of the substrate material in an etchant solution including a fluoride etchant such as hydrofluoric acid (HF) and an oxidizing agent such as hydrogen peroxide ($H_2O_2$).

Substrate material including silicon (Si) is preferred. However, substrate materials can include germanium (Ge), arsenic (As), selenium (Se), gallium (Ga), tellurium (Te), polonium (Po), and combinations thereof, as well as mixtures of group III, IV, and V compounds such as Ga—As, Si—C, Ga—N, Si—N, Ga—Si, and Si—As. Substrate materials can also be doped with a dopant such as, but not limited to, boron (B), phosphorous (P), arsenic (As), gallium (Ga).

Metal catalysts can include, but are not limited to, gold (Au), silver (Ag), platinum (Pt), tungsten (W), palladium (Pd), copper (Cu), and combinations and/or alloys thereof. Other metal catalysts can also include aluminum (Al), titanium (Ti), Nickel (Ni), iron (Fe), zinc (Zn), cadmium (Cd), indium (In), tin (Sn), antimony (Sb), tellurium (Te), lead (Pb), bismuth (Bi), vanadium (V), chromium (Cr), manganese (Mg), ruthenium (Ru), molybdenum (Mo), and other transition metals. Fluoride etchants also include, but are not limited to, buffered oxide etch (BOE), boron hydrogen fluoride (BHF), or other fluoride complex (e.g., $BF_4-$, $PF_6-$, $CF_3SO_3-$, $AsF_6-$, and $SbF_6-$). Other oxidizing agents that can be used include, but are not limited to, $K_2MnO_4$ and $FeNO_3$.

In exemplary embodiments, the growth density of the nanowires 16 on the growth surface is from one to a few nanowires (e.g., 1 to 10, 1 to 3, up to 15). In other applications, many nanowires 16 may be desirable (e.g., up to 50 or up to 75). The total conductance between the originating surface on an electrode and the contacted surface on another electrode depends on density of nanoparticles, diameter of nanowires and the size of electrodes from which the wires are growing. A higher density of nanoparticles on the growth surface results in a higher density of nanowires, which generally results in a higher total conductance.

Nanoparticle sizes, and thus the resulting radial diameters, are in the range of less than 100 nm, alternatively 1 to 5 nm, and alternatively 5 to 50 nm, and further alternatively less than 40 nm. In exemplary embodiments, the diameter of the nanowire 16 is sufficient to have diffusion lengths and diffusion kinetics of the dopant species to allow desired switching times at a programming temperature, e.g., greater than or equal to about 700° C. to 800° C., preferably at or above 800° C. up to or above 1000° C., which is much greater than the operating temperature, e.g., from room temperature to about 100° C.

The programming temperature is at least partially dependent on the semiconductor material of the nanowire. For example, a programming temperature for Si is greater than about 800° C. Also, a nanowire dimension can be configured small enough for rapid diffusion and short diffusion times at a programming temperature and slow diffusion and long diffusion times at operating temperatures. It is noted that programming time is proportional to diffusion length (L), where $L=2\sqrt{(Dt)}$. D is the diffusion coefficient, and t is the time at elevated temperature during which the dopant atoms can move within the nanowire. In exemplary embodiments, the diffusion length (L) is less than about 1 µm, alternatively less than 100 nm, 50 nm, 40 nm or 10 nm. The diameter can be selected to be compatible with a desired programming speed. It is noted that faster speed can result from a smaller diameter as well as result from programming at higher programming temperature, or a combination of these approaches.

In various embodiments, the materials and layers can be deposited by physical vapor deposition (PVD), chemical vapor deposition (CVD), atomic layer deposition (ALD), molecular beam epitaxy (MBE), or any of the various modifications thereof, for example plasma-enhanced chemical vapor deposition (PECVD), metal-organic chemical vapor deposition (MOCVD), low pressure chemical vapor deposition (LPCVD), electron-beam physical vapor deposition (EB-PVD), and plasma-enhanced atomic layer deposition (PE-ALD). The depositions can be epitaxial processes, and the deposited material can be crystalline. In various embodiments, formation of a layer can be by one or more deposition processes, where, for example, a conformal layer can be formed by a first process (e.g., ALD, PE-ALD, etc.) and a fill can be formed by a second process (e.g., CVD, electrodeposition, PVD, etc.).

Figure 4:
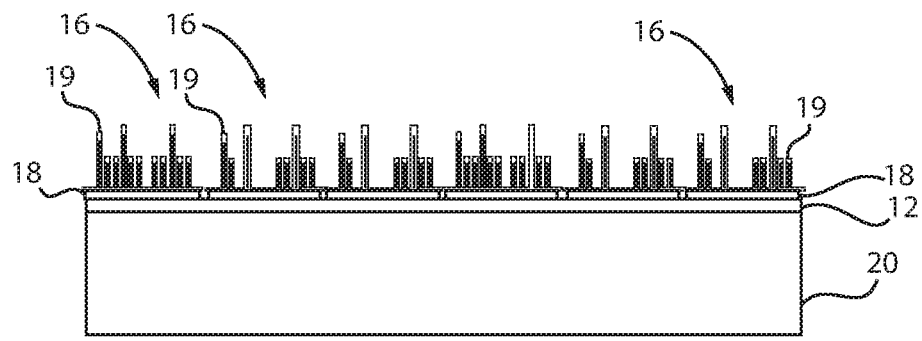
FIG. 4 is a cross-sectional view of the semiconductor structure of FIG. 3 where a conducting layer is deposited over the plurality of Si nanowires, in accordance with an embodiment of the present invention.

FIG. 4 is a cross-sectional view of the semiconductor structure of FIG. 3 where a conducting layer is deposited over the plurality of Si nanowires, in accordance with an embodiment of the present invention.

In various embodiments, a metal layer 19 is deposited and the substrate 14 is broken into a plurality of substrates 18, each substrate 18 configured to accommodate a plurality of nanowires 16 coated with metal layer 19. The metal layer coating 19 enhances biocompatibility and improves the mechanical strength of the nanowires 16. Metal deposition methods can include, e.g., PVD, plating, evaporation, etc. The metal layer 19 can be, e.g., a biocompatible metal, such as titanium nitride (TiN).

Figure 5:
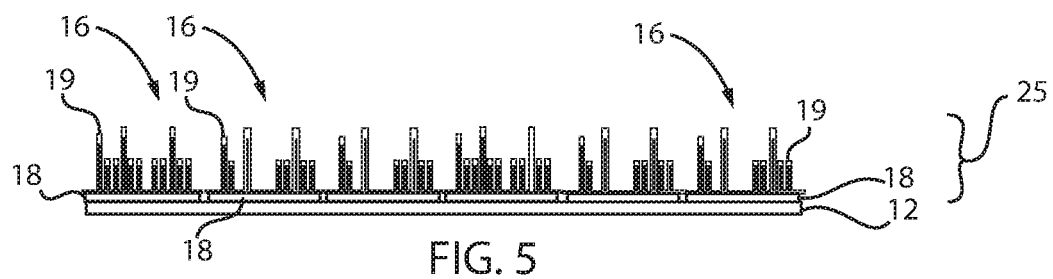
FIG. 5 is a cross-sectional view of the semiconductor structure of FIG. 4 where the glass handler is removed, in accordance with an embodiment of the present invention.

FIG. 5 is a cross-sectional view of the semiconductor structure of FIG. 4 where the glass handler is removed, in accordance with an embodiment of the present invention.

In various embodiments, the glass handler 20 is removed, thus leaving behind a plurality of nanowire electrodes 25 placed over the bonding layer 12.

Figure 6:
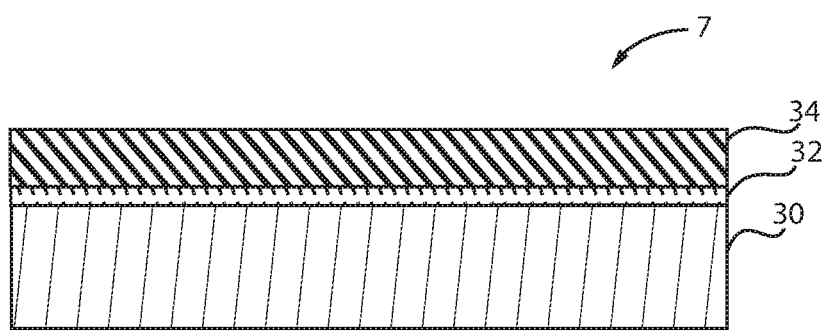
FIG. 6 is a cross-sectional view of another semiconductor structure where a flexible polymer substrate is attached to another glass handler, in accordance with an embodiment of the present invention.

FIG. 6 is a cross-sectional view of another semiconductor structure where a flexible polymer substrate is attached to another glass handler, in accordance with an embodiment of the present invention.

A semiconductor structure 7 includes a polymer layer 34 attached to a glass handler 30 via a release layer 32. The release layer assists the glass handler releasing process, and the polymer layer 34 can be used as a flexible substrate of the final nanowire electrode, as described further below.

Figure 7:
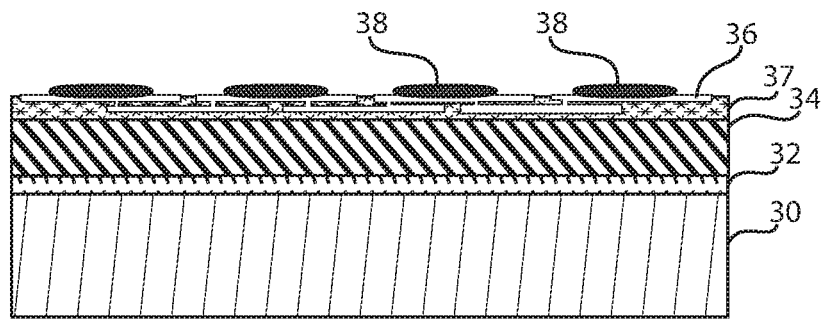
FIG. 7 is a cross-sectional view of the semiconductor structure of FIG. 6 where interconnection lines are formed within the flexible substrate and solder bumps are deposited adjacent the interconnection lines, the solder bumps used to join nanowire chips to the flexible substrate, in accordance with an embodiment of the present invention.

FIG. 7 is a cross-sectional view of the semiconductor structure of FIG. 6 where interconnection lines are formed within the flexible substrate and solder bumps are deposited adjacent the interconnection lines, the solder bumps used to join nanowire chips to the flexible substrate, in accordance with an embodiment of the present invention.

In various embodiments, conducting lines 36 are fabricated within a polymer layer 37 deposited over the flexible polymer layer 34. Additionally, solder bumps 38 are deposited over the conducting lines 36. The solder bumps 38 do not contact each other. The solder bumps 38 are separated from each other by a predetermined distance. The conducting lines 36 can be metal lines. The metal lines 36 can be used as electrical interconnections between nanowire chips. The solder bumps 38 can be used to join the nanowire chips to the flexible polymer substrate 34. The solder bumps 38 can also be referred to as solder nanodots or solder films or solder ball bumps.

Figure 8:
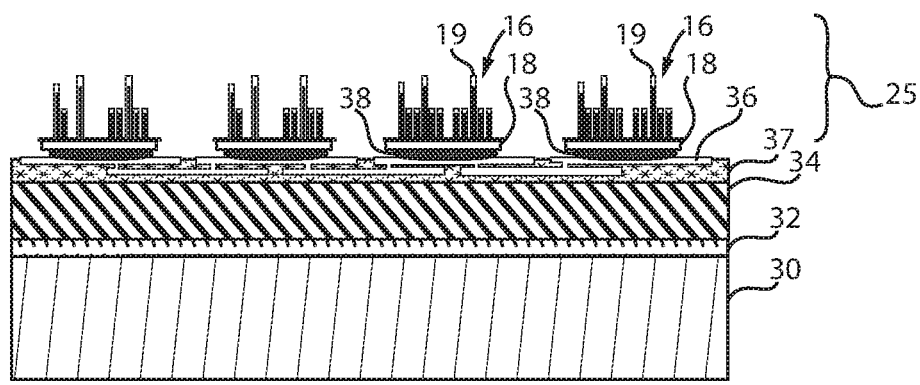
FIG. 8 is a cross-sectional view of the semiconductor structure of FIG. 7 where the electrode arrays of FIG. 4 are integrated with the solder bumps, in accordance with an embodiment of the present invention.

FIG. 8 is a cross-sectional view of the semiconductor structure of FIG. 7 where the electrode arrays of FIG. 4 are integrated with the solder bumps, in accordance with an embodiment of the present invention.

In various embodiments, the electrodes 25 of FIG. 5 are attached to the solder bumps 38 such that each electrode array 25 is associated with a single solder bump 38. The electrodes 25 are attached such that respective solder bumps 38 contact the respective substrate 18 of each of the electrode arrays 25. The solder bumps 38 separate the metal lines 36 from the electrode arrays 25.

Figure 9:
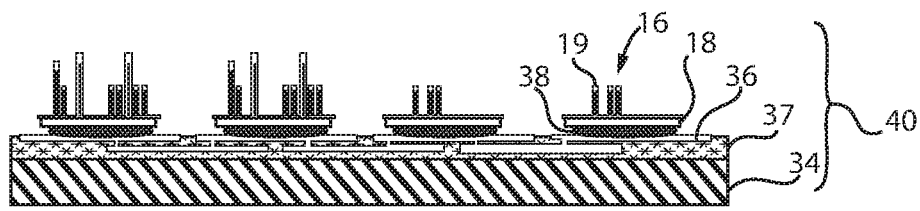
FIG. 9 is a cross-sectional view of the semiconductor structure of FIG. 8 where the glass handler is released, in accordance with an embodiment of the present invention.

FIG. 9 is a cross-sectional view of the semiconductor structure of FIG. 8 where the glass handler is released, in accordance with an embodiment of the present invention.

In various embodiments, the glass handler 30 and the release layer 32 are removed, thus leaving behind a plurality of nanowire electrodes 25 placed over the flexible substrate 34. The nanowire structure 40 is ready to be applied to the skin of a subject, e.g., a patient. The silicon nanowires coated with a metal layer are configured to penetrate the skin of a patient. Specifically, the silicon nanowires are designed to penetrate at least the stratum germinativum (SG) layer (or stratum basale layer) of the skin, as described further below with reference to FIG. 11.

Figure 10:
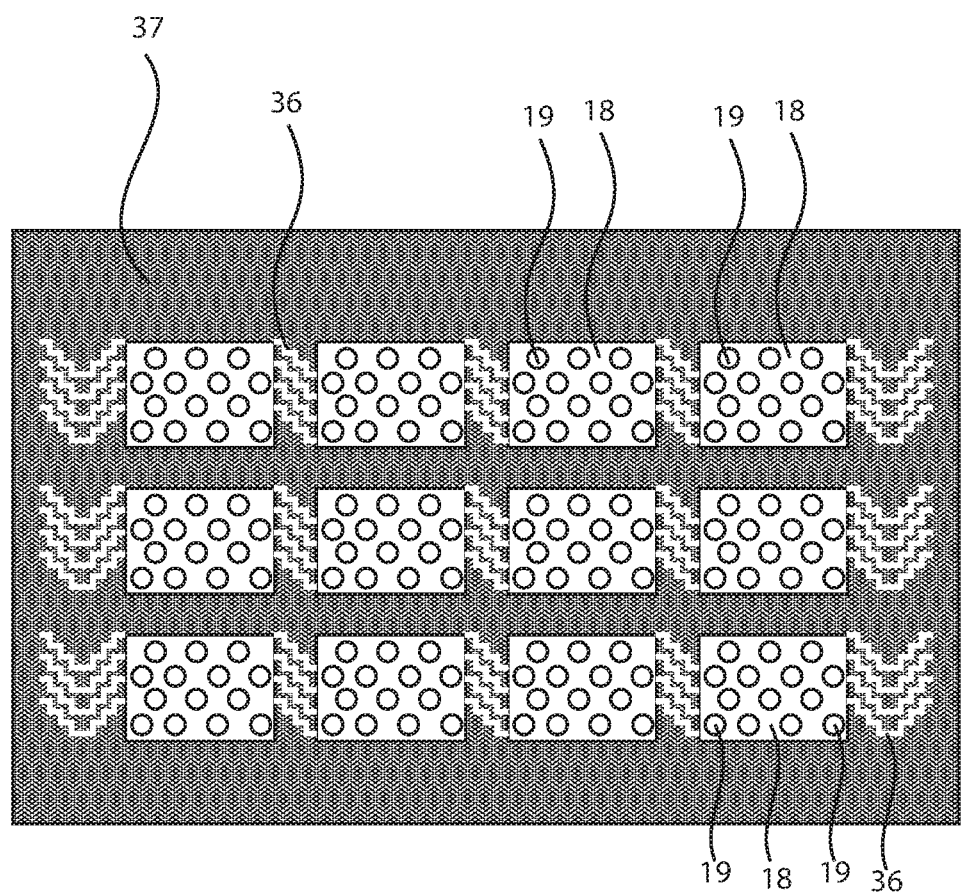
FIG. 10 is a top view of the semiconductor structure of FIG. 9, in accordance with an embodiment of the present invention.

FIG. 10 is a top view of the semiconductor structure of FIG. 9, in accordance with an embodiment of the present invention.

The top view illustrates each electrode array. The top coated surface 19 of the nanowires 16 is showed surrounded by substrates 18. Metal lines 36 are also shown connecting the electrode arrays 25 to each other.

Figure 11:
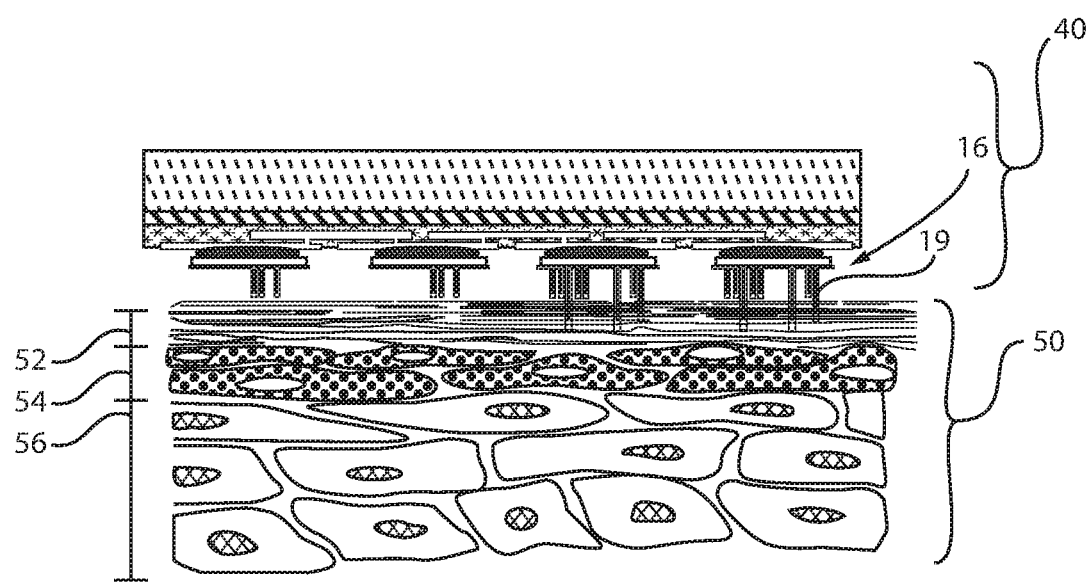
FIG. 11 is a perspective view of the flexible silicon nanowire electrode of FIG. 9 in contact with skin of a subject, in accordance with an embodiment of the present invention.

FIG. 11 is a perspective view of the flexible silicon nanowire electrode of FIG. 9 in contact with skin of a subject, in accordance with an embodiment of the present invention.

In various embodiments, the nanowire structure 40 is used to penetrate the skin 50 of a subject. The skin 50 is composed of three basic layers or regions. The first layer 52 is the epidermis. The second layer 54 is the dermis. The third layer 56 is the hypodermis. The first layer 52 includes 5 different layers. These layers are the stratum corneum layer, the stratum lucidum layer, the stratum granulosum layer, the stratum spinosum layer, and the stratum basale layer (also referred to as the stratum germinativum layer). The stratum basale layer contacts the dermis region 54. The dermis region can include two different layers, that is, the papillary region and the reticular region. Therefore, the stratum basale layer is adjacent the dermis region 54 or the farthest away from the outer surface of the skin of the subject, yet within the epidermis region 52.

The nanowires 16 coated with the metal layer 19 are configured to penetrate the skin 50 such that the nanowires 16 reach at least the stratum germinativum layer of the epidermis 52 adjacent the dermis 54. Thus, the nanowires 16 extend to a distalmost region of the epidermis 52 (i.e., the stratum basale layer or stratum germinativum layer). As a result, the silicon nanowires penetrate the electrically conductive stratum germinativum (SG) layer to circumvent the high impedance at the skin sensor interface. The stratum germinativum (SG) layer can be approximately 50-100 µm deep.

Figure 12:
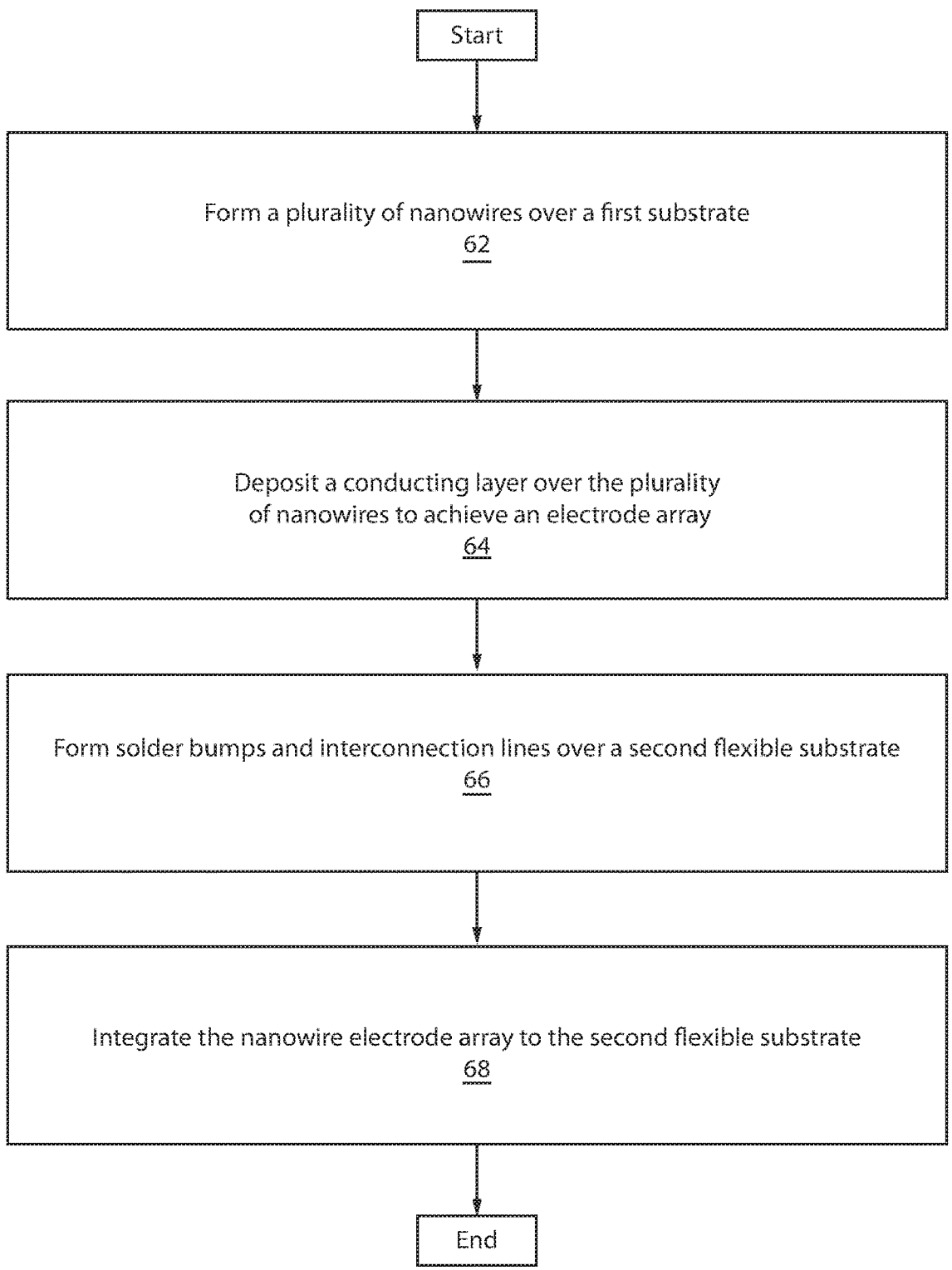
FIG. 12 is a block/flow diagram of an exemplary method for forming a flexible silicon nanowire electrode, in accordance with an embodiment of the present invention.

FIG. 12 is a block/flow diagram of an exemplary method for forming a flexible silicon nanowire electrode, in accordance with an embodiment of the present invention.

At block 62, a plurality of nanowires are formed over a first substrate.

At block 64, a conducting layer is deposited over the plurality of nanowires to achieve an electrode array.

At block 66, solder bumps and interconnection lines are formed over a second flexible substrate.

At block 68, the nanowire electrode array is integrated with the second flexible substrate.

The nanostructures of the exemplary embodiments have been illustratively shown to be used for medical device applications. However, the nanostructures of the exemplary embodiments of the present invention can be used in many applications including, but not limited to, solar cells, light emitting diodes (LEDs), laser diodes (LDs) such as distributed feedback (DFB) lasers and distributed Bragg reflector (DBR) lasers, detectors, field effect transistors (FETs), thermoelectric devices, sensors such as along biological interfaces, and nanoscale processing units.

Methods as described herein can be used in the fabrication of integrated circuit chips and/or solar cells. The resulting integrated circuit chips or cells can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes photovoltaic devices, integrated circuit chips with solar cells, ranging from toys, calculators, solar collectors and other low-end applications to advanced products for medical applications, as described herein.

It is to be understood that the present invention will be described in terms of a given illustrative architecture; however, other architectures, structures, substrate materials and process features and steps/blocks can be varied within the scope of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical mechanisms (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present embodiments. The compounds with additional elements will be referred to herein as alloys.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a method of device fabrication and a semiconductor device thereby fabricated to form a flexible silicon nanowire electrode (which are intended to be illustrative and not limiting), it is noted that modifications and variations can be made by persons skilled in the art in light of the above teachings. It is therefore to be understood that changes may be made in the particular embodiments described which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method of forming a nanowire electrode, the method comprising:
    forming a plurality of nanowires over a first substrate;
    depositing a conducting layer over the plurality of nanowires to form nanowire electrode arrays on the first substrate;
    forming electrical interconnections over a flexible second substrate;
    forming solder over the electrical interconnections; and
    integrating the nanowire electrode arrays of the first substrate to the flexible second substrate by removing the first substrate from the nanowire electrode arrays and integrating the nanowire electrode arrays with the solder formed over the electrical interconnections on the flexible second substrate.

2. The method of claim 1, wherein the first substrate is a silicon (Si) substrate and the flexible second substrate is a flexible polymer substrate.

3. The method of claim 1, wherein the plurality of nanowires are silicon (Si) nanowires, the Si nanowires used as probes to penetrate at least a stratum basale layer of skin of a subject.

4. The method of claim 1, wherein the conducting layer is a titanium nitride (TiN) layer.

5. The method of claim 1, wherein the plurality of nanowires are formed over the first substrate by metal-assisted chemical etching.

* * * * *